(12) United States Patent
Manzer

(10) Patent No.: US 7,465,813 B2
(45) Date of Patent: Dec. 16, 2008

(54) PROCESS FOR MAKING 5-METHYL-N-ALKYL-2-PYRROLIDONE FROM ALKYL AMINE(S) AND LEVULINIC ACID

(75) Inventor: Leo Ernest Manzer, Wilmington, DE (US)

(73) Assignee: E. I. Du Pont de Nemours + Company, Wilmington, DE (US)

( * ) Notice: Subject to any disclaimer, the term of this patent is extended or adjusted under 35 U.S.C. 154(b) by 450 days.

(21) Appl. No.: 11/115,534

(22) Filed: Apr. 27, 2005

(65) Prior Publication Data

US 2006/0247444 A1 Nov. 2, 2006

(51) Int. Cl.
*C07D 207/267* (2006.01)

(52) U.S. Cl. ...................................... 548/554

(58) Field of Classification Search ................. 192/215, 192/223, 223.1, 15, 16, 43.1, 45.1; 188/134; 548/554

See application file for complete search history.

(56) References Cited

U.S. PATENT DOCUMENTS

| 3,235,632 | A  | * | 2/1966 | Lemmer et al. ............. 264/521 |
| 6,900,337 | B2 | * | 5/2005 | Manzer et al. .............. 548/554 |
| 2004/0192933 | A1 | | 9/2004 | Manzer et al. |
| 2005/0054861 | A1 | | 3/2005 | Manzer |

\* cited by examiner

*Primary Examiner*—Kamal A Saeed
(74) *Attorney, Agent, or Firm*—Karin Karet

(57) ABSTRACT

This invention relates to a process for producing a reaction product comprising 5-methyl-N-alkyl-2-pyrrolidone by (a) reacting levulinic acid with alkyl amine(s) and (b) hydrogenating the products of step (a) in the presence of a metal catalyst, which is optionally supported.

14 Claims, No Drawings

PROCESS FOR MAKING 5-METHYL-N-ALKYL-2-PYRROLIDONE FROM ALKYL AMINE(S) AND LEVULINIC ACID

FIELD OF INVENTION

This invention relates to a process for producing a reaction product comprising 5-methyl-N-alkyl-2-pyrrolidone by (a) reacting levulinic acid with at least one alkyl amine and (b) hydrogenating the products of step (a) in the presence of a metal catalyst, which is optionally supported.

BACKGROUND OF THE INVENTION

N-Alkyl-pyrrolidones can act as solvents, surfactants, dispersants, detergents and emulsifiers, and thus are useful in a wide variety of applications. N-Alkyl-pyrrolidones are components, for example, in cleaners such as industrial, metal and surface cleaners, paint strippers, printing inks, gasoline and oil additives, industrial coatings and detergents. N-Alkyl-pyrrolidones are also useful in oil and gas well maintenance, polymer synthesis, photoresist applications, agricultural and pharmaceutical manufacture and paper manufacture.

U.S. Patent Appl. No. 2005/0054861 describes a process for producing 5-methyl-N-alkyl-2-pyrrolidone by a) reacting α-angelica lactone with alkyl amines, and b) hydrogenating the products of step (a) in the presence of a metal catalyst. α-Angelica lactone has limited availability and thus does not represent a cost-effective starting material for this reaction.

U.S. Patent Appl. No. 2004/0192933 describes a one-step process for preparing 5-methyl-1-$R^1$-2-pyrrolidone comprising contacting levulinic acid with a primary amine.

The present invention provides an alternative method for preparing 5-methyl-N-alkyl-2-pyrrolidone.

SUMMARY OF THE INVENTION

The present invention relates to a process for making a reaction product comprising 5-methyl-N-alkyl-2-pyrrolidone. The process comprises the steps of (a) contacting levulinic acid with at least one alkyl amine, optionally in the presence of an inert solvent, and (b) reacting the products of step (a) with hydrogen gas in the presence of a hydrogenation catalyst to produce a reaction product comprising 5-methyl-N-alkyl-2-pyrrolidone, wherein the alkyl group is selected from —$CH_3$, —$CH_2OH$, —$C_2H_5$, —$C_2H_4OH$, straight-chain, branched or cyclic $C_3$ to $C_{25}$ alkyl, straight-chain, branched or cyclic $C_3$ to $C_{25}$ alkyl comprising at least one hydroxyl group, and straight-chain, branched or cyclic $C_3$ to $C_{25}$ alkyl comprising at least one heteroatom selected from the group consisting of O and N.

DETAILED DESCRIPTION OF THE INVENTION

The present invention relates to a process for preparing a reaction product comprising 5-methyl-N-alkyl-2-pyrrolidone by a process that comprises the steps of (a) contacting levulinic acid with at least one alkyl amine, optionally in the presence of an inert solvent, and (b) reacting the products of step (a) with hydrogen gas in the presence of a hydrogenation catalyst. Without wishing to be bound by any particular theory, the step (a) reaction is believed to produce a number of intermediates comprising at least one of those shown in the following reaction scheme, and these intermediates are believed to be converted by hydrogenation to the final product, namely the 5-methyl-N-alkyl-2-pyrrolidone.

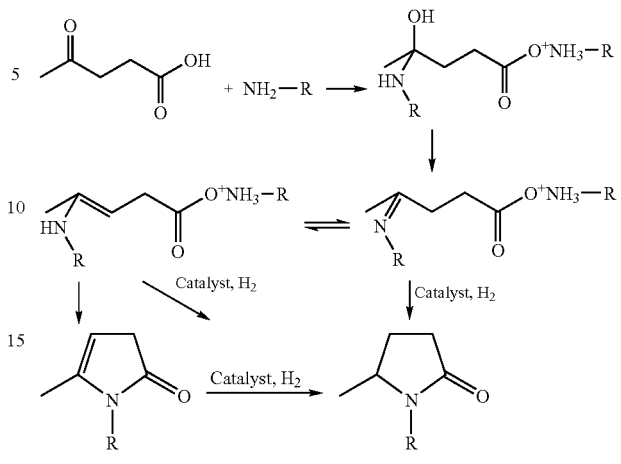

In the reaction scheme shown above, R may be selected from the group consisting of —$CH_3$, —$CH_2OH$, —$C_2H_5$, —$C_2H_4OH$, straight-chain, branched or cyclic $C_3$ to $C_{25}$ alkyl, straight-chain, branched or cyclic $C_3$ to $C_{25}$ alkyl comprising at least one hydroxyl group, and straight-chain, branched or cyclic $C_3$ to $C_{25}$ alkyl comprising at least one heteroatom selected from the group consisting of O and N.

A catalyst, with or without a support, must be present in the process of the invention to effect the hydrogenation step (b). The hydrogenation catalyst may be a metal selected from the group consisting of nickel, copper, cobalt, iron, rhodium, ruthenium, rhenium, osmium, iridium, platinum, palladium, at least one Raney® metal; compounds thereof; and combinations thereof. A catalyst support optionally may be used. A promoter such as, without limitation, tin, zinc, copper, gold, silver and combinations thereof may be used to affect the reaction, for example, by increasing activity and catalyst lifetime.

The molar ratio of the alkyl amine to levulinic acid preferably is from about 0.1:1 to about 10:1 at the start of the reaction. Preferably, step (a) is performed at a temperature of from about 0° C. to about 150° C., and step (b) is performed at a temperature of from about 50° C. to about 250° C. In another embodiment, step (a) is performed at room temperature (about 25° C.). Preferably step (b) of the reaction is performed at a hydrogen pressure of from about 0.34 MPa to about 20.0 MPa. In another embodiment, step (b) of the reaction is performed at about 0.34 MPa to about 3.5 MPa.

The process of the present invention may be carried out in batch, sequential batch (i.e., a series of batch reactors) or in continuous mode in any of the equipment customarily employed for continuous processes.

In a preferred embodiment of the invention, R is selected from the group consisting of —$CH_3$, —$C_2H_5$, straight-chain, branched or cyclic $C_3$ to $C_{12}$ alkyl, and straight-chain, branched or cyclic $C_3$ to $C_{12}$ alkyl comprising at least one heteroatom selected from the group consisting of O and N.

The reaction of the present invention can be performed in an inert solvent such as ethers (e.g. dioxane), straight-chain, branched or cyclic $C_5$ to $C_{30}$ alkanes (e.g. hexane), and aromatics (e.g. toluene). Preferably the reaction is carried out without a solvent.

The catalyst used in the hydrogenation step (b) may be supported or unsupported. A supported catalyst is one in which the catalytic metal is deposited on a support material by any one of a number of methods, such as spraying, soaking or physical mixing, followed by drying, calcination, and if necessary, activation through methods such as reduction or oxidation/reduction. Materials frequently used as a support are porous solids with high total surface areas (external and internal) which can provide high concentrations of active sites per unit weight of catalyst. The catalyst support may enhance the function of the catalyst.

A catalyst that is not supported on a catalyst support material is an unsupported catalyst. An unsupported catalyst may be platinum black or a Raney® catalyst (W.R. Grace Company). Raney® catalysts have a high surface area due to selectively leaching an alloy containing the active metal(s) and a leachable metal (usually aluminum). Raney® catalysts have high activity due to the higher specific area and allow the use of lower temperatures in hydrogenation reactions. The active metals of Raney® catalysts include nickel, copper, cobalt, iron, rhodium, ruthenium, rhenium, osmium, iridium, platinum, palladium; compounds thereof; and combinations thereof.

Promoter metals may also be added to the base Raney® metals to affect selectivity and/or activity of the Raney® catalyst. Promoter metals for Raney® catalysts may be selected from transition metals from Groups IIIA through VIIIA, IB and IIB of the Periodic Table of the Elements. Examples of promoter metals include chromium, molybdenum, platinum, rhodium, ruthenium, osmium, and palladium, typically at about 2% by weight of the total metal.

The catalyst support useful herein can be any solid, inert substance including, but not limited to, oxides such as silica, alumina, titania, and combinations thereof; barium sulfate; calcium carbonate; carbons; and combinations thereof. The catalyst support can be in the form of powder, granules, pellets, or the like.

In the processes of the invention, the preferred content of the metal catalyst in a supported catalyst is from about 0.1% to about 20% of the supported catalyst based on metal catalyst weight plus the support weight. A more preferred metal catalyst content range is from about 1% to about 10% of the supported catalyst. A further preferred metal catalyst content range is from about 3% to about 7% of the supported catalyst.

Combinations of catalyst and support system may include any one of the metals referred to herein with any of the supports referred to herein. Examples include palladium on carbon, palladium on calcium carbonate, palladium on barium sulfate, palladium on alumina, palladium on titania, platinum on carbon, platinum on alumina, platinum on silica, iridium on silica, iridium on carbon, iridium on alumina, rhodium on carbon, rhodium on silica, rhodium on alumina, nickel on carbon, nickel on alumina, nickel on silica, rhenium on carbon, rhenium on silica, rhenium on alumina, ruthenium on carbon, ruthenium on alumina and ruthenium on silica. Preferred combinations of catalyst and support include palladium on carbon, platinum on carbon, iridium on carbon, rhodium on carbon, ruthenium on carbon, iridium on silica, and combinations thereof.

The following examples are illustrative of the invention.

EXAMPLES

The following abbreviations are used: SCCM, standard cubic centimeters per minute; GC-MS, gas chromatography-mass spectrometry; ° C., degrees Centigrade; g, gram; min, minute; hr, hour; ml, milliliter; MPag, mega Pascal gauge.

For preparation of Ir/silica gel, silica (Grade 55; W. R. Grace, Columbia, Md.) was impregnated by incipient wetness with $IrCl_3 3H_2O$ (Alfa Aesar, Ward Hill, Mass.). The sample was dried and reduced at about 450° C. under $H_2$ for 2 hours.

Levulinic acid, nonylamine, heptylamine and ethanolamine are available from Sigma-Aldrich (St. Louis, Mo.); Platinum black was obtained from Alfa Aesar; ESCAT-142 was obtained from Engelhard Corp. (Iselin, N.J.).

Examples 1-7

Preparation of 5-Methyl-N-Alkyl-2-Pyrrolidone

Levulinic acid (LA) and the indicated alkyl amine ($R$—$NH_2$) were mixed in approximately equal molar equivalents at room temperature (~25° C.) to prepare a solution. To this solution was added the unsupported (Platinum black) or supported metal catalyst. The reactor was pressurized with hydrogen at the indicated pressure and heated for 1 hr. At the end of the reaction, the reactor was cooled, vented and the product analyzed by GC-MS using an HP 6890 (Agilent; Palo Alto, Calif.) equipped with a WCOT fused silica column, 25 m×0.25 MM ID, coating CP-wax 58 (FFAP)-CB DF=0.2 (Varian, Palo Alto, Calif.).

R-Pyr refers to the product 5-methyl-N-alkyl-2-pyrrolidone prepared using the indicated alkyl amine.

| Ex. No. | Catalyst | R—NH$_2$ | Temp (° C.) | H$_2$ Pressure (MPa) | Molar Ratio Acid/R—NH$_2$ | LA (g) | R—NH$_2$ (g) | Catalyst (g) | R-Pyr Yield (%) |
|---|---|---|---|---|---|---|---|---|---|
| 1 | Escat 142 (5% Pd/C) | Nonylamine | 150 | 0.827 | 0.50 | 2.88 | 7.12 | 1.00 | 81.80 |
| 2 | Escat 142 (5% Pd/C) | Nonylamine | 225 | 0.310 | 0.50 | 2.88 | 7.12 | 1.00 | 65.10 |
| 3 | Escat 268 (5% Pt/C) | Heptylamine | 150 | 0.621 | 0.50 | 3.35 | 6.65 | 1.02 | 76.32 |
| 4 | Escat 268 (5% Pt/C) | Heptylamine | 150 | 0.621 | 1.1 | 5.02 | 4.98 | 1.07 | 80.15 |
| 5 | Platinum Black | Heptylamine | 150 | 0.621 | 1.1 | 5.02 | 4.98 | 1.07 | 59.79 |
| 6 | 5% Ir/Silica Gel | Heptylamine | 150 | 0.621 | 1.1 | 5.02 | 4.98 | 1.06 | 69.05 |
| 7 | Escat 142 (5% Pd/C) | Ethanolamine | 150 | 0.621 | 1.1 | 6.55 | 3.45 | 1.05 | 29.98 |

What is claimed is:

1. A process for making a reaction product comprising 5-methyl-N-alkyl-2-pyrrolidone comprising the steps of (a) contacting levulinic acid with at least one alkyl amine, optionally in the presence of an inert solvent, and (b) reacting the products of step (a) with hydrogen gas in the presence of a hydrogenation catalyst to produce the 5-methyl-N-alkyl-2-pyrrolidone, wherein the alkyl group of the alkyl amine is selected from —$CH_3$, —$CH_2OH$, —$C_2H_5$, —$C_2H_4OH$, straight-chain, branched or cyclic $C_3$ to $C_{25}$ alkyl, straight-chain, branched or cyclic $C_3$ to $C_{25}$ alkyl comprising at least one hydroxyl group, and straight-chain, branched or cyclic $C_3$ to $C_{25}$ alkyl comprising at least one heteroatom selected from the group consisting of O and N.

2. The process as recited in claim 1, wherein the catalyst is selected from metals selected from the group consisting of nickel, copper, cobalt, iron, rhodium, ruthenium, rhenium, osmium, iridium, platinum, palladium, at least one Raney® metal; compounds there; of and combinations thereof.

3. The process as recited in claim 2, wherein the catalyst is palladium or compounds thereof.

4. The process as recited in claim 2, wherein the catalyst is supported and the content of the metal in the supported metal catalyst is from 0.1% to 20% by weight.

5. The process as recited in claim 4, wherein the catalyst support is selected from the group consisting of oxides of silica, alumina, titania and combinations thereof barium sulfate; calcium carbonate; carbons; and combinations thereof.

6. The process as recited in claim 1, wherein the catalyst is augmented with a promoter.

7. The process as recited in claim 1 wherein the process is carried out in the absence of a solvent.

8. The process as recited in claim 1, wherein the alkyl group of the alkyl amine is selected from the group consisting of —$CH_3$, —$C_2H_5$, straight-chain, branched or cyclic $C_3$ to $C_{12}$ alkyl, and straight-chain, branched or cyclic $C_3$ to $C_{12}$ alkyl comprising at least one heteroatom selected from the group consisting of O and N.

9. The process as recited in claim 1, wherein the molar ratio of the alkyl amine to levulinic acid preferably is from about 0.1:1 to about 10:1 at the start of the reaction.

10. The process as recited in claim 9, wherein step (a) is performed at a temperature of from about 0° C. to about 150° C., and step (b) is performed at a temperature of from about 50° C. to about 250° C.

11. The process as recited in claim 10, wherein step (b) is performed at a hydrogen pressure of from about 0.34 MPa to about 20.0 MPa.

12. The process as recited in claim 4, wherein the supported metal catalyst is selected from the group consisting of palladium on carbon, palladium on calcium carbonate, palladium on barium sulfate, palladium on alumina, palladium on titania, platinum on carbon, platinum on alumina, platinum on silica, iridium on silica, iridium on carbon, iridium on alumina, rhodium on carbon, rhodium on silica, rhodium on alumina, nickel on carbon, nickel on alumina, nickel on silica, rhenium on carbon, rhenium on silica, rhenium on alumina, ruthenium on carbon, ruthenium on alumina and ruthenium on silica.

13. The process as recited in claim 12, wherein the supported metal catalyst is selected from the group consisting of palladium on carbon, platinum on carbon, iridium on carbon, rhodium on carbon, ruthenium on carbon, iridium on silica, and combinations thereof.

14. The process as recited in claim 1, wherein the alkyl group of the alkyl amine is selected from the group consisting of —$CH_3$, —$CH_2OH$, —$C_2H_5$, —$C_2H_4OH$, straight-chain, branched or cyclic $C_3$ to $C_{25}$ alkyl, straight-chain, branched or cyclic $C_3$ to $C_{25}$ alkyl comprising at least one hydroxyl group, and straight-chain, branched or cyclic $C_3$ to $C_{25}$ alkyl comprising at least one heteroatom selected from the group consisting of O and N ; the catalyst is supported and the supported catalyst is palladium on carbon; the temperature of step (a) of the reaction is from about 0° C. to about 150° C., the temperature of step (b) of the reaction is from about 50° C. to 250° C., and the pressure of step (b) of the reaction is from about 0.34 MPa to about 20.0 MPa.

* * * * *